United States Patent [19]

Bennani et al.

[11] Patent Number: 5,609,851
[45] Date of Patent: Mar. 11, 1997

[54] COMPOUNDS WHICH CAN BE USED IN CONTRAST PRODUCTS FOR RADIOGRAPHY

[75] Inventors: Fatima Z. Bennani, Paris; Soizic le Greneur, Bures-Sur-Yvette; Christian Simonot, Paris; Dominique Meyer, Saint-Maur, all of France

[73] Assignee: Guerbet S A., Villepinte, France

[21] Appl. No.: 290,920

[22] PCT Filed: Feb. 22, 1993

[86] PCT No.: PCT/FR93/00175

§ 371 Date: Nov. 21, 1994

§ 102(e) Date: Nov. 21, 1994

[87] PCT Pub. No.: WO93/16983

PCT Pub. Date: Sep. 2, 1993

[30] Foreign Application Priority Data

Feb. 24, 1992 [FR] France .................................. 92 02112

[51] Int. Cl.$^6$ .......................... A61K 49/04; C07C 233/05
[52] U.S. Cl. ......................................... 424/9.454; 564/153
[58] Field of Search ........................ 424/9.454; 564/153

[56] References Cited

U.S. PATENT DOCUMENTS 4,547,357 10/1985 Pfeiffer et al. .............................. 424/5
5,043,152 8/1991 Schaefer et al. ........................... 424/5

FOREIGN PATENT DOCUMENTS 0049745 4/1982 European Pat. Off. .
0082803 12/1982 European Pat. Off. .
0185130 3/1985 European Pat. Off. .
3429949 2/1986 Germany .

OTHER PUBLICATIONS

T. Nakanishi, "Hydrophilic Elastomers", Chemical Abstracts, vol. 88, No. 4, Jan. 23, 1978, Abstract No. 24102c.

*Primary Examiner*—Shailendra Kumar
*Attorney, Agent, or Firm*—Jacobson, Price, Holman & Stern, PLLC

[57] ABSTRACT

Polyiodinated nonionic compound that have the formula:

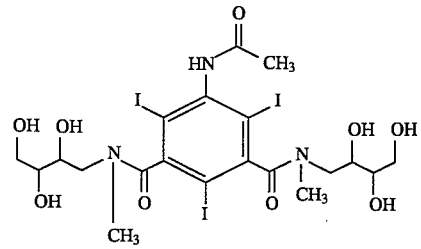

3 Claims, No Drawings

COMPOUNDS WHICH CAN BE USED IN CONTRAST PRODUCTS FOR RADIOGRAPHY

This application is a 371 of PCT/FR93/00175, filed Feb. 22, 1993.

The present invention relates to compounds which can be used in contrast media for radiography.

BACKGROUND

Iodobenzene compounds having on the benzene ring several iodine atoms, in general 3 iodine atoms per benzene ring and various other substituents, have been used for a long time as contrast agents. These other substituents are pharmacologically acceptable groups which allow administration of the compounds to man and to animals. These substituents are generally chosen, on the one hand, to confer on the compounds a sufficient water-solubility for administering these compounds in aqueous solution and, on the other hand, to confer on these compounds sufficient tolerance by the human body.

To this effect, nonionic compounds, that is to say substituted iodobenzenes possessing nonionic substituents, have been proposed.

SUMMARY OF THE INVENTION

The object of the present invention is to provide new nonionic compounds which are well tolerated by the human body, which are stable in aqueous solution, which possess good water-solubility and which, in aqueous solution, possess low viscosity.

To this effect, the present invention provides compounds having formula I:

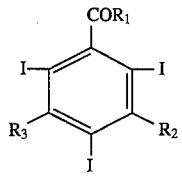

wherein:

$R_1$ represents a group selected from

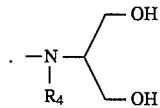

$R_4$ representing —CH$_3$, —CH$_2$—CH$_2$OH, —CH$_2$—CHOH—CH$_2$OH or —CH—(CH$_2$OH)$_2$,

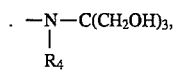

$R_4$ being as defined above,

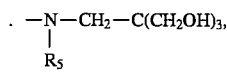

$R_5$ representing —H or $R_4$,

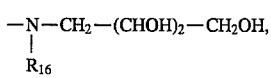

$R_{16}$ representing $R_4$ or —CH$_2$(CHOH)$_2$CH$_2$OH

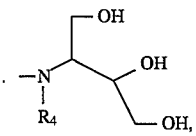

$R_4$ being as defined above,

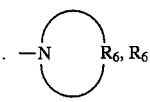

representing a linear or branched (C$_4$–C$_8$)alkylene group, a linear or branched hydroxy- or polyhydroxy (C$_1$—C$_4$)alkylene group, a linear or branched (C$_1$–C$_4$)alkoxy(C$_4$–C$_8$)alkylene group, a linear or branched hydroxy- or polyhydroxdroxy(C$_1$–C$_4$)alkoxy(C$_4$–C$_8$)alkylene group, $R_2$ represents a group selected from —COR$_1$ and

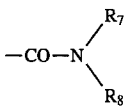

$R_1$ being as defined above and $R_7$ and $R_8$, which are identical or different, representing a group selected from —H, a linear or branched (C$_1$–C$_6$)alkyl, a linear or branched hydroxy- or polyhydroxy(C$_1$–C$_6$)alkyl group, a linear or branched (C$_1$–C$_4$)alkoxy(C$_1$–C$_6$)alkyl group and a linear or branched hydroxy- or polyhydroxy(C$_1$–C$_4$)alkoxy(C$_1$–C$_6$)alkyl group, $R_3$ represents
the group

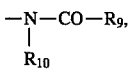

$R_9$ and $R_{10}$ representing $R_7$ and $R_8$, a group of formula

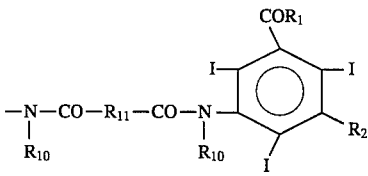

a group of formula

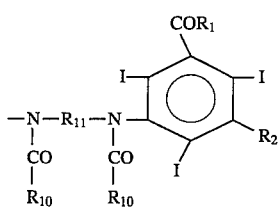

$R_{10}$ being as defined above and $R_{11}$ having the seine meanings as $R_{10}$ except —H.

DESCRIPTION OF THE PREFERRED EMBODIMENTS

Polyhydroxy group is understood to mean a group containing 2 to 5 —OH groups.

Among the preferred

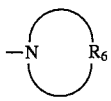

groups, there may be mentioned those possessing 2 to 4 hydroxyl groups and containing 5 to 6 members, especially: the groups

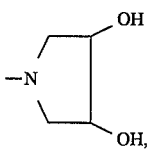

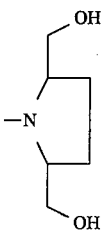

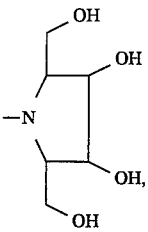

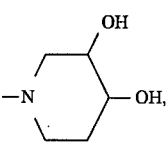

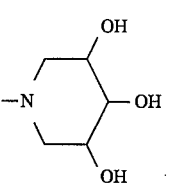

and

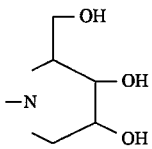

A first group of preferred compounds according to the invention is that having the following formula II:

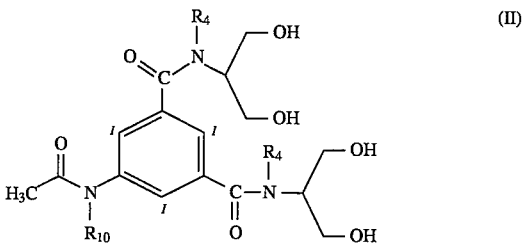

wherein $R_4$ is —CH$_2$CH$_2$OH or —CH$_2$—CHOH—CH$_2$OH and $R_{10}$ is —H or —CH$_3$.

The compound of the following formula IIa is particularly preferred:

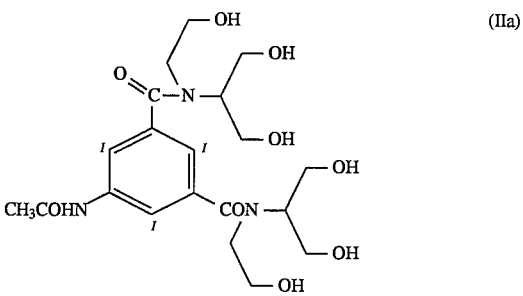

A second group of preferred compounds according to the invention is that having the following formula III:

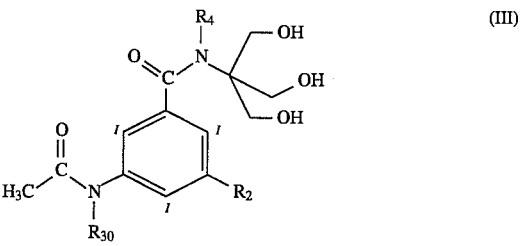

wherein $R_2$ is

—CO—NH—CH$_3$,

—CO—NH—CH$_2$—CH$_2$OH or

—CO—N—C(CH$_2$OH)$_3$,
       |
       $R_4$ $R_4$ is as defined above for formula I, and $R_{10}$ represents —H or —CH$_3$.

The compounds of the following formula IIIa, IIIb, IIIc, IIId and IIIe are particularly preferred:

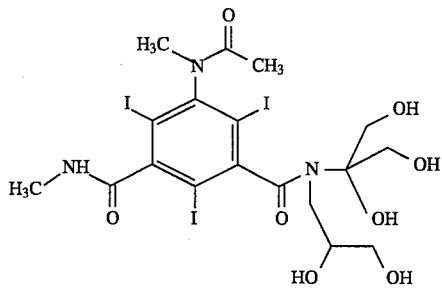
IIIa

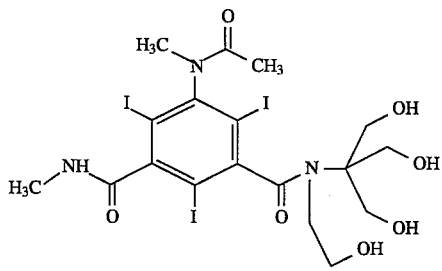
IIIb

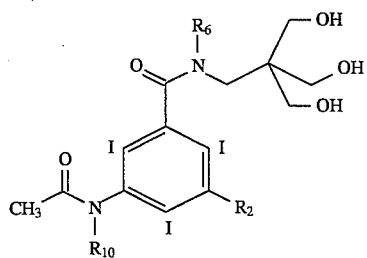
IIIc

IIId

IIIe

A third group of preferred compounds according to the invention is that having the following formula IV:

(IV)

wherein $R_2$ is selected from the groups

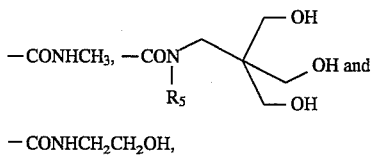

—CONHCH$_3$, —CON

—CONHCH$_2$CH$_2$OH, $R_5$ is as defined above for the formula I and $R_{10}$ represents —H or —CH$_3$.

The compounds of the following formula IVa, IVb, IVc, IVd, IVe and IVf are particularly preferred:

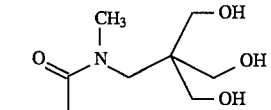 IVa

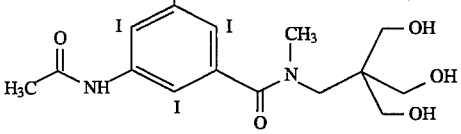

IVb

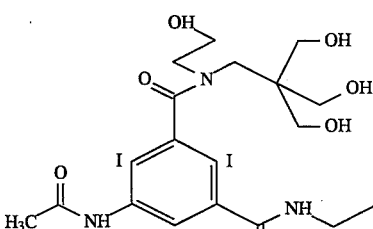

IVc

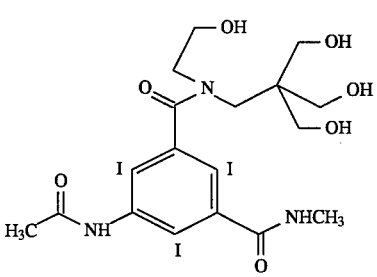

IVd

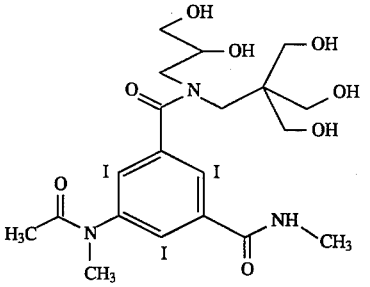

IVe

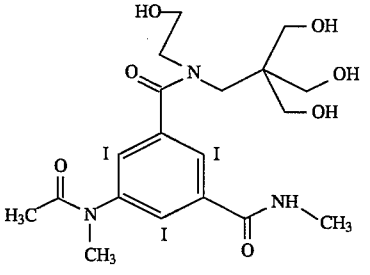

-continued

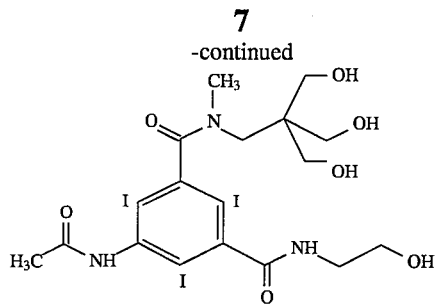    IVf

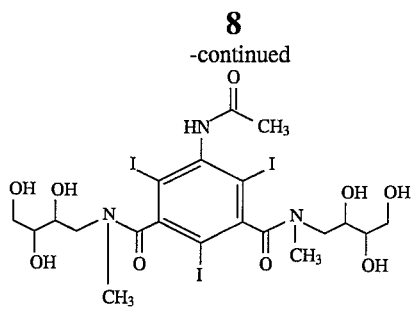    Vc

A fourth group of preferred compounds according to the invention is that having the following formula V:

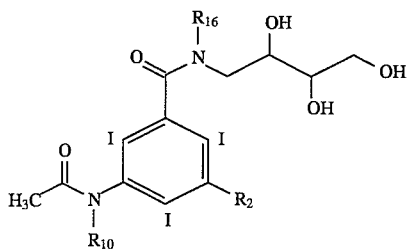

wherein:

R$_2$ is —CONHCH$_3$,

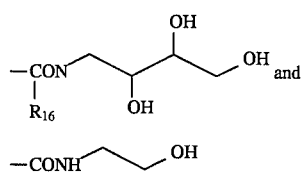 and

R$_{16}$ is as defined above for the formula I and R$_{10}$ represents —H or —CH$_3$.

The compounds of the following formulae Va, Vb, Vc, Vd and Ve are particularly preferred:

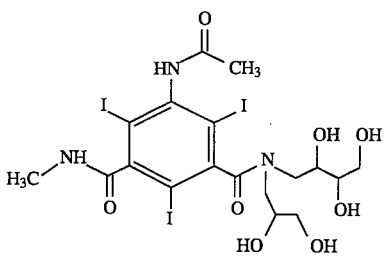    Va

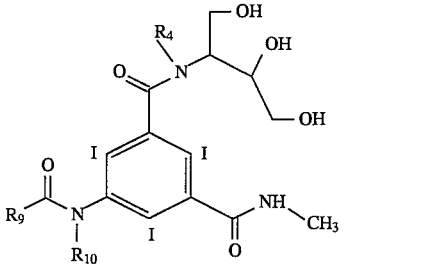    Vd

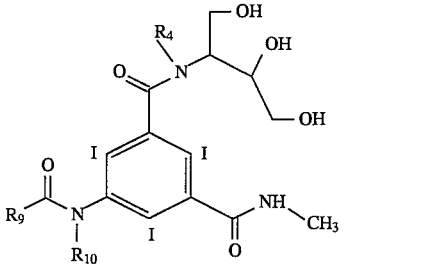    Ve

A fifth group of preferred compounds according to the invention is that having the following formula VI:

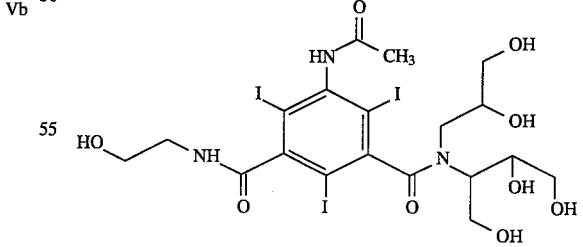    (VI)

wherein R$_4$ is as defined above for the formula I, R$_9$ represents —CH$_3$ or —CH$_2$CH$_2$OH and R$_{10}$ represents —H or —CH$_3$. The compounds of the following formulae VIa and VIb are particularly preferred:

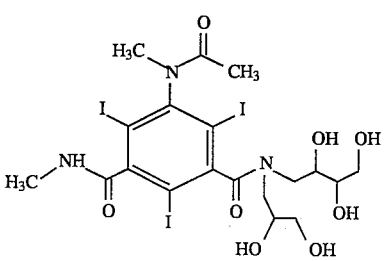    Vb (VIa)

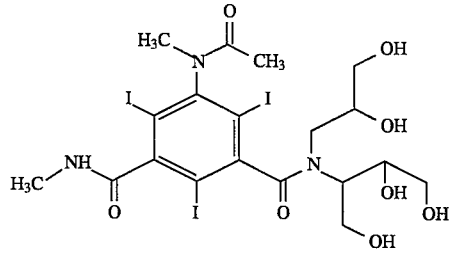

A sixth group of preferred compounds according to the invention is that having the formula VII below:

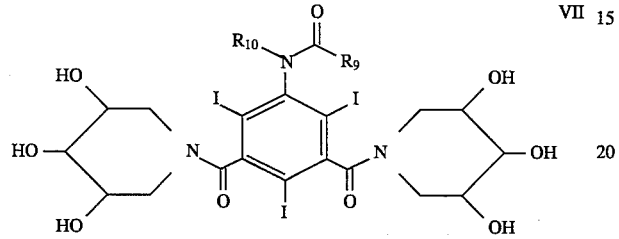

wherein $R_9$ and $R_{10}$ are as defined for the formula I.

Among the compounds of the invention which contain a cyclic amine, another preferred product is:

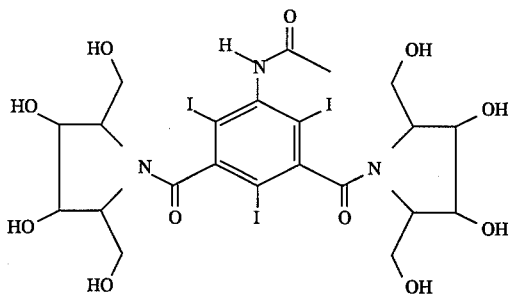

Among the compounds of the invention of the dimeric type the products of formulae below are preferred:

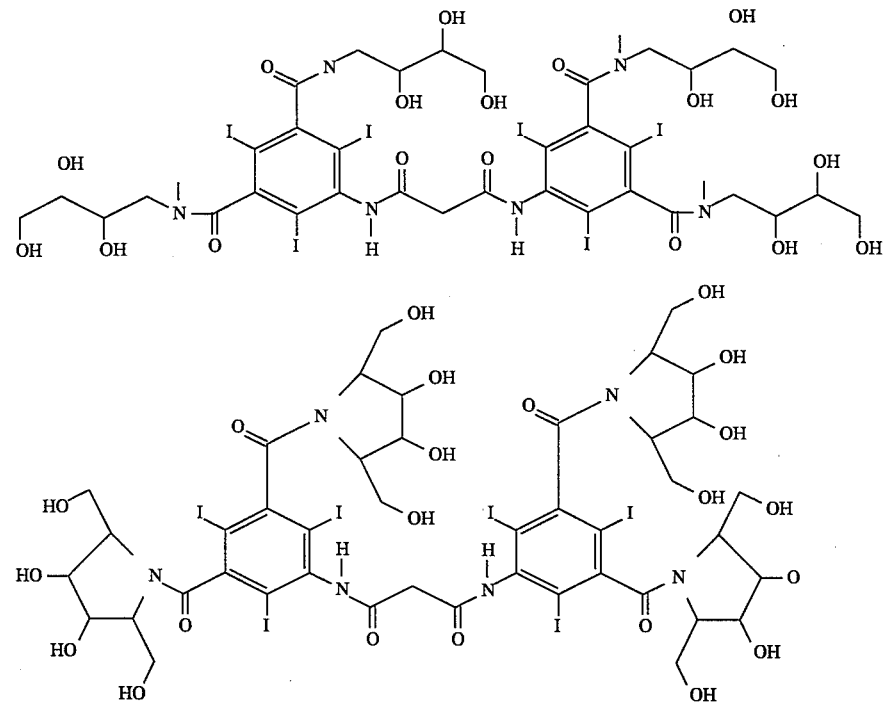

The compounds of formula I in which the group $R_2$ is different from the group —$COR_1$ may be advantageously prepared by the process consisting of the following stages:

a) reduction, under usual conditions, of a compound of formula VIII

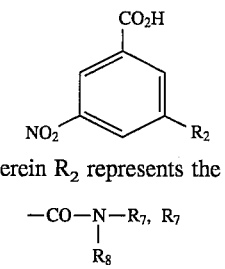
(VIII)

wherein $R_2$ represents the group

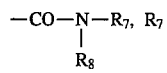

and $R_8$ are as defined above for the formula I, to give a compound of formula IX

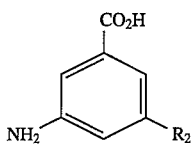
(IX)

$R_2$ being as defined above, b) iodination of the compound of formula IX to give a compound of formula X:

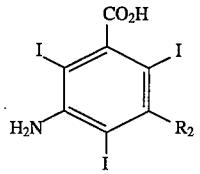
(X)

wherein $R_2$ is as defined above c) optionally, protection of the hydroxyl groups of $R_2$ by means of a conventional protecting group; and, $d_1$) chlorination of the compound of formula X, under usual conditions, to give a compound of formula XI:

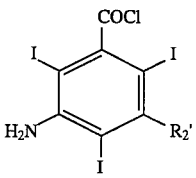
(XI)

wherein $R'_2$ represents the group $R_2$, optionally protected, $e_1$) acylation of the compound of formula XI under usual conditions, by means of a compound of formula XII:

$R'_9COCl$ (XII)

wherein $R'_9$ represents $R_9$ whose hydroxyl groups are protected, to give a compound of formula XIII:

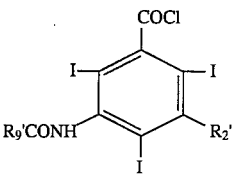
(XIII)

wherein $R'_9$ and $R'_2$ are as defined above, $f_1$) amidation of the compound of formula XIII, under usual conditions, with an aminoalcohol selected from the compounds of formula:

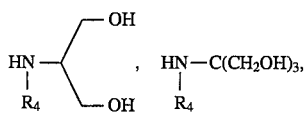

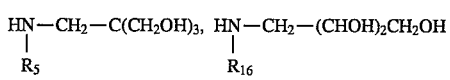

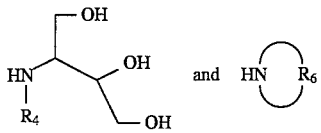

$R_4$, $R_5$, $R_6$ and $R_{16}$ being as defined above for the formula I, to give a compound of formula XIV:

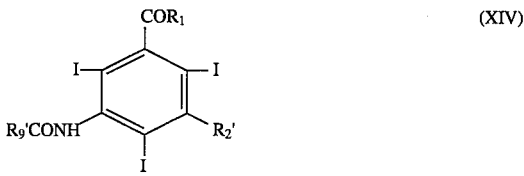
(XIV)

wherein $R'_2$, $R'_9$ and $R_1$ are as defined above, $g_1$) optionally, deprotection of the hydroxyl groups of $R'_2$ and $R'_9$, and $h_1$) optionally, alkylation, under usual conditions, of the compound of formula XIV with a compound of the formula XV:

$R_{10}-X$ (XV)

$R_{10}$ being as defined above and X being a movable group such as Br, Cl or I, to give a compound of formula I.

The compounds of formula I in which $R_2=-COR_1$, $R_1$ and $R_3$ being as defined above for the formula I, can also be prepared in the following manner:

a) reduction, under usual conditions, of a compound of formula XVI:

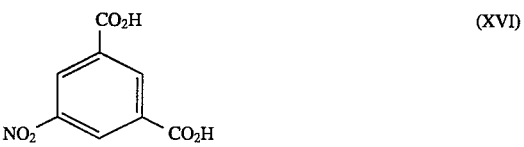
(XVI)

to give a compound of formula XVII:

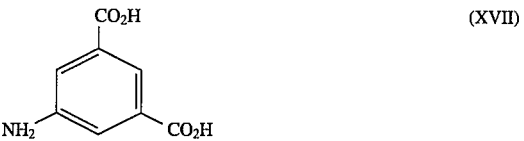
(XVII)

b) iodination of the compound of formula XVII to give the compound of formula XVIII:

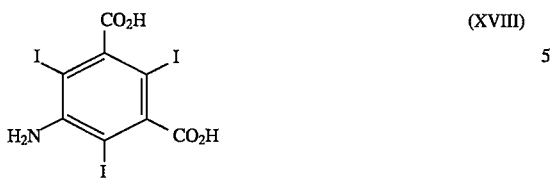

c) chlorination under usual conditions, of the compound of formula XVIII to give the compound of formula XIX:

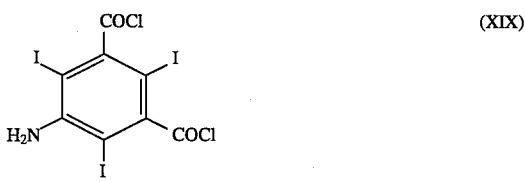

d) acylation of the compound of formula XIX under usual conditions, by means of a compound of formula XII, as defined above, to give a compound of formula XX:

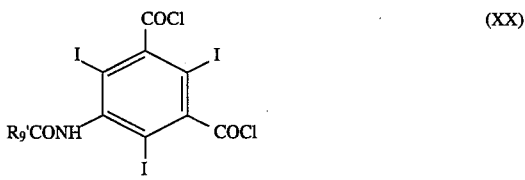

R'$_9$ being as defined above, e) amidation of the compound of formula XX, under usual conditions, with an aminoalcohol selected from

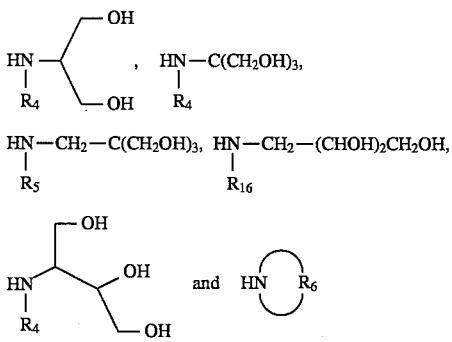

R$_4$, R$_5$, R$_6$ and R$_{16}$ being as defined above for the formula I, so as to give a compound of formula XXI:

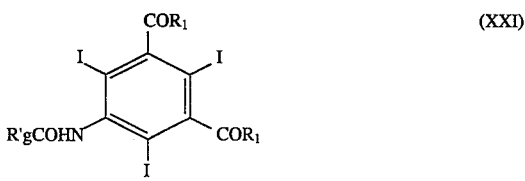

in which R$_1$ and R'$_9$ are as defined above.

f) optionally, deprotection of the hydroxyl groups of R'$_9$
g) optionally, alkylation, under usual conditions, of the compound of formula XXI with a compound of formula XV as defined above, to give a compound of formula I.

The compound of formula VIII is obtained according to the method described in the patent FR-no. 6777M.

The reaction of stage a) is advantageously carried out by catalytic reduction by hydrogen over palladised carbon or over Raney nickel or by chemical reduction under usual conditions.

The iodination step is carried out under usual conditions such as by means of aqueous ICl or I$_2$, in the presence of KI/ethylamine or KICl$_2$, at temperatures ranging from 0° C. to 100° C.

The chlorination reactions are carried out in the usual manner, for example by means of SOCl$_2$ or PCl$_5$ at high temperature.

The acylation reactions are advantageously carried out in a solvent such as DMAC.

The amidation reactions are advantageously carried out in the presence of triethylamine.

The reactions for deprotecting the hydroxyl groups are advantageously carried out in the presence of K$_2$CO$_3$ in methanol or NaOH, H$_2$SO$_4$ or HCl.

The reaction for alkylating the compound of formula IX is advantageously carried out in the presence of NaOH, KOH, MeONa in DMAC, DMF or monoglyme.

The acetylation reaction is preferably carried out using acetic anhydride in a solvent, in the presence of pyridine, HClO$_4$, H$_2$SO$_4$, DMAP or using acetyl chloride at high temperature.

The compounds of formula VII are prepared by the process described above from 5-acetamido-2,4,6-triiodo-isophthaloyl dichloride and the aminoalcohol of formula

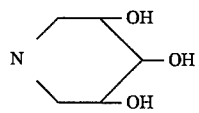

The subject matter of the invention is also new aminoalcohols which are intermediate products in the preparation of test products for diagnosis. The aminoalcohols are especially useful as agents which enhance the biocompatibility of in particular iodinated contrast products, and more particularly the compounds of formula I.

A first group of new aminoalcohols have the following formula:

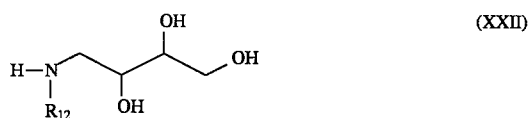

in which R$_{12}$ represents a group selected from —CH$_3$, —CH$_2$CH$_2$OH, —CH$_2$—CHOH—CH$_2$OH, —CH—(CH$_2$OH)$_2$ and —CH$_2$(CHOH)$_2$—CH$_2$OH.

A second group of new aminoalcohols have the following formula XXIII:

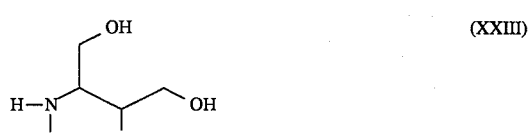

in which R$_{13}$ is selected from —CH$_3$, —CH$_2$CH$_2$OH, —CH$_2$—CHOH—CH$_2$OH, and —CH(CH$_2$OH)$_2$.

A third group of new aminoalcohols have to the following formula XXIV:

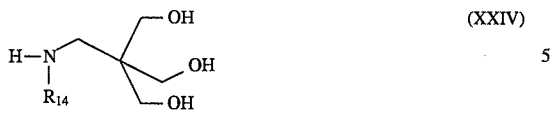
(XXIV)

in which $R_{14}$ is a group selected from —$CH_3$, —$CH_2CH_2OH$ and —$CH_2CHOHCH_2OH$.

The preparation of the following aminoalcohols will be described below:

aminoalcohol of formula XXII in which $R_{12}$ represents —$CH_3$ (compound no. 1), aminoalcohol of formula XXII in which $R_{12}$ represents the group —$CH_2CHOH$—$CH_2OH$ (compound no. 2), aminoalcohol of formula XXII in which $R_{12}$ represents the group $CH_2CHOH$ (compound no. 3), aminoalcohol of formula XXII in which $R_{12}$ represents —$CH(CH_2OH)_2$ (compound no. 4), aminoalcohol of formula XXIII in which $R_{13}$ represents

(compound no. 5)

aminoalcohol of formula XXIII in which $R_{13}$ represents —$CH_3$ (compound no. 6), aminoalcohol of formula XXIII in which $R_{13}$ represents —$CH_2CH_2OH$ (compound no. 7), aminoalcohol of formula XXIII in which $R_{13}$ represents —$CH(CH_2OH)_2$ (compound no. 8), aminoalcohol of formula XXIV in which $R_{14}$ represents the group —$CH_3$ (compound no. 9), aminoalcohol of formula XXIV in which $R_{14}$ represents —$CH_2CH_2OH$ (compound no. 10), aminoalcohol of general formula XXIV in which $R_{14}$ represents the group —$CH_2$—(CHOH)—$CH_2OH$ (compound no. 11), aminoalcohol of formula XXII in which $R_{12}$ represents —$CH_2$—$(CHOH)_2$—$CH_2OH$ (compound no. 12).

Preparation of the aminoalcohol no. 1

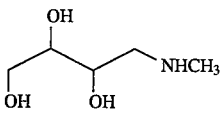

a) Preparation of the compound of formula

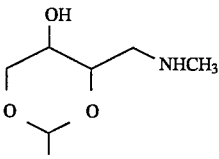

2 g (13.7 mmol) of 2,4-ethylidene-D-erythrose obtained according to the process described in J. Am. Chem. Soc. 2301, 1960, Barker R. et al., are dissolved in 10 cm³ of water at 30° C. 10 cm³ of an aqueous solution of methylamine (40%) are added dropwise at 0° C. After returning to room temperature, the stirring is continued for 2 h. The solution is then reduced, at room temperature, in the presence of palladium on carbon. The catalyst is then filtered and the filtrate concentrated to dryness. After solidification in ethyl ether, 1.7 g of the title product are obtained, equivalent to a yield of 77%.

TLC (dioxane/$H_2O$/$NH_3$:8/3/2) Rf: 0.74
TLC ($CH_2Cl_2$/MeOH 8/2) Rf: 0.17.
$^{13}C$ NMR (DMSO) (δ,ppm) 200 MHz 98.2—(C—CH); 80.3 (CH—O); 70.5 (CH_2—O); 63.4 (CHOH); 53.1 (CH_2—N); 36.5 (NH—CH_3); 20.7 (C—CH_3).

b) Preparation of the compound of formula:

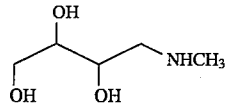

1.5 g (9.3 mmol) of the product obtained in a) are dissolved in 20 cm³ of 2N HCl. The solution is stirred at 50° C. for 5 h. After concentration, and purification by passing through an H⁺ resin, the solution is evaporated to dryness. The residue is taken up in ethyl ether. After filtration and drying, 0.8 g of the title product is obtained (yield: 64%).

TLC (dioxane/$H_2O$/$NH_3$:8/3/2) Rf: 0.18
$^{13}C$ NMR (DMSO) (δ,ppm):200 MHz 74.5—(CH—CH_2OH); 69.6 (CHOHCH_2); 63.3 (—CH_2OH); 54.7 (—CH_2); 36.12 (NHCH_3) MS (DCI/$NH_3$) m/z: 153 (M+N⁺H_4); 136 (M+H⁺) base peak.

Preparation of the aminoalcohol no. 2

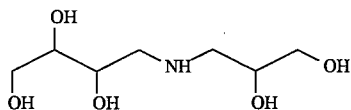

a) Preparation of the compound of formula:

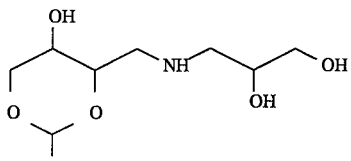

The compound is prepared according to the method described above.

The amino-reduction of 2,4-ethylidene-D-erythrose (6 g, 41 mmol) is carried out in the presence of aminopropanediol (1.2 equiv.) in ethanol (40 cm³).

After chromatography on a silica column, the title product is obtained with a yield of 73%.

TLC (dioxane/$H_2O$/$NH_3$:8/3/2) Rf: 0.73 $^{13}C$ NMR (DMSO) (δ,ppm):(200 MHz) (98, C —CH_3); (80.2–80.5, CH—O); (70.2–70.4 CH_2—O); (70.3.CHOH); (64.5–64.6, CH_2OH); (62.2–63.1, CHOH);(52.9–53, CH_2); (50.8–51, CH_2); (20.5, CH_3).

b) Preparation of the compound of formula:

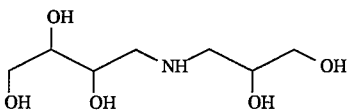

6 g (29.8 mmol) of the product obtained in the preceding stage are deprotected by treatment with 5N HCl (50cm³). The reaction medium is stirred for 4 h at 50° C. After evaporation, the residue obtained is purified on an H⁺ resin. After concentration and solidification in ethyl ether, 2.6 g of the title product are obtained (yield 54.7%)

TLC (dioxane/$H_2O$/$NH_3$:8/3/2) Rf: 0.39
$^{13}C$ NMR (DMSO) (δ,ppm) 74.3 (CH—CH_2OH butanetriol chain); 70.3 (CH—CH_2)×2; 64.5–64.6 (CH_2OH butanetriol chain); 63.3 (CH_2OH); 52.8 (CH_2N)×2

MS (DCI/NH$_3$) m/z 196 (M+H$^+$) base peak;178 (M+H$^+$—H$_2$O); 160 (M+H$^+$—2H$_2$O) 136, 122, 109, 92.

Preparation of the aminoalcohol no. 3

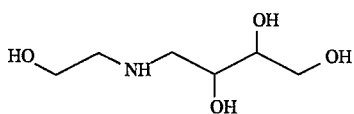

Just like methylamine (for the preparation of the aminoalcohol no. 1) and aminopropanediol (for the preparation of the aminoalcohol no. 2), ethanolamine, under the same amino-reduction conditions, gives, presence of 2,4-ethylidene-D-erythrose, the title product.

a) Preparation of the compound of formula

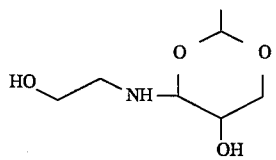

TLC(CH$_2$Cl$_2$/MeOH/NH$_3$:8/2/1) Rf: 0.56

$^{13}$C NMR (DMSO) (δ,ppm): 97.9 (C—CH$_3$); 80.5 (CH—O); 70.2 (CH$_2$OH); 62.9 (CHOH); 60.2 (CH$_2$—O); 51.6(CH$_2$—N); 50.7 (CH$_2$—N); 20.4 (CH$_3$).

b) Preparation of the compound of formula

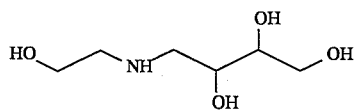

TLC(CH$_2$Cl$_2$/MeOH/NH$_2$ 55/30/10) Rf: 0.25
TLC(dioxane/H$_2$O/NH$_3$:8/3/2) Rf: 0.48

$^{13}$C NMR (DMSO) (δ,ppm): 74.5 (CHOHCH$_2$OH); 70.2 (CHOH—CH$_2$); 63.5 (CHOHCH$_2$OH); 60.4 (CH$_2$CCH$_2$OH); 52.5 (CH$_2$—CHOH); 51.8 (CH$_2$CH$_2$OH).

By repeating the procedures described above and by using serinol with 2,4-ethylidene-D-erythrose, the aminoalcohol of formula

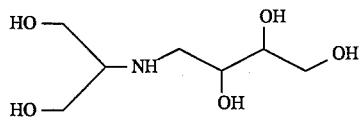

(aminoalcohol no. 4) is obtained.

Preparation of the aminoalcohol no. 5

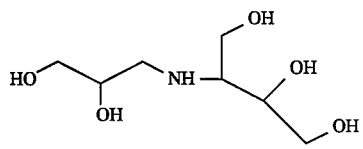

3 g (18 mmol) of 2,3-epoxy-1,4-butyldiol prepared according to the method described in J. Med. Chem. 1976, vol. 19, No. 1, 153–158, are dissolved in 10 cm$^3$ of methanol. 0.9 equiv. of aminopropanediol in 10 cm of methanol is added dropwise, at room temperature. The reaction medium is maintained at 45°–50° C. for 48 h. After evaporation, the crude product is purified with an H$^+$ resin and concentrated to dryness. After taking up in ether and drying, 4 g of the title product are obtained (yield 72.7%).

TLC (dioxane/H$_2$O/NH$_3$:8/3/2) Rf: 0.58 (CH$_2$Cl$_2$/MeOH/NH$_3$: 6/3/1) Rf: 0.55

$^{13}$C NMR (DMSO) (δ,ppm): 71–71.2 (CHOH);64.6(—NH—CH—CH$_2$OH); 63.5 (CH$_2$OH propanediol chain); 61.4 (—CH—); 61 (CH$_2$OH); 51.3 (CH$_2$—N).

The opening of the epoxide described above can also be performed using methylamine, ethanolamine and serinol so as to obtain, respectively, the compounds:

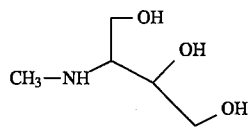

aminoalcohol no. 6

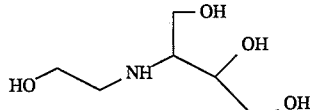

aminoalcohol no. 7

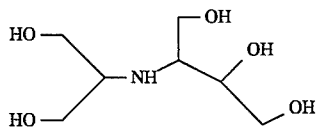

aminoalcohol no. 8

Preparation of the aminoalcohol of formula:

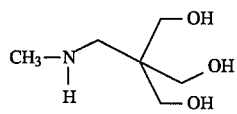

(aminoalcohol no. 9)

18.1 g (0.1 mol) of 3-bromomethyl-3-hydroxymethyloxetane, prepared according to the method described in Propellants, Explos., Pyrotech., 16(1)40–42, 1991, are stirred in 20 ml of methanol and 76 ml (1 mol) of 40% aqueous methylamine at 50° C., for 24 h The mixture is evaporated to dryness and the residue is dissolved in 100 ml of 0.1N sulphuric acid.

The solution is refluxed for 12 h and then treated by a resin. The title product is obtained by evaporation of the eluent.

Preparation of the aminoalcohol of formula no. 10:

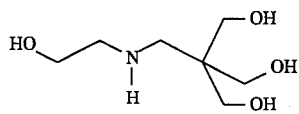

18.1 g (0.1 mol) of 3-bromomethyl-3-hydroxymethyloxetane, obtained as described above are stirred in 20 ml of methanol and 60.5 ml (1 mol) of ethanolamine at 50° C., for 24 h. The mixture is evaporated to dryness and the residue is dissolved in 100 ml of 0.1N sulphuric acid. The solution is refluxed for 12 h and then treated by a resin. The title compound is obtained by evaporation of the eluent.

In the same manner as for the aminoalcohols nos. 9 and 10, the aminoalcohol no. 11 of formula:

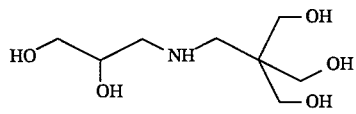

is obtained from 3-bromoethyl-3-hydroxymethyloxetane and 1-amino-2,3-propanediol.

Preparation of the aminoalcohol no. 12:

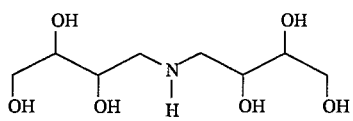

3,4-butanediol is prepared according to the rearrangement method described in patent U.S. Pat. No. 4,661,646 from 1,4-butanediol (available, commercially from the company Aldrich-Strasbourg).

Epoxidation of the 3,4-butanediol is carried out according to the method described in patent U.S. Pat. No. 3,352,898 and gives 3,4-epoxy-1,2-butanediol.

The opening of the epoxy diol with benzylamine (0.5 equiv.) gives bis(2,3,4-trihydroxybutyl)benzylamine.

After debenzylation, by hydrogen, in the presence of palladised carbon, bis(2,3,4-trihydroxybutyl)amine(aminoalcohol no. 12) is obtained.

The aminoalcohol of formula

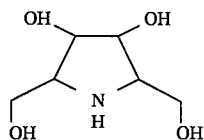

is prepared as described in Tetrahedron Letters, 31, 6777 (1990), J. Org. Chem. 50, 892 (1985) or J. Chem. Soc. Chem. Commun. 262 (1987).

The aminoalcohol of formula XXIII, in which $R_{13}$ represents H, is prepared as described in U.S. Pat. No. 4,341,756 and U.S. Pat. No. 4,439,613.

The aminoalcohol of formula XXV

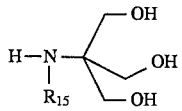 (XXV)

in which $R_{15}$ represents —$CH_3$ is prepared as described in J. Org. Khim., 22 (2), 298, 1986.

The aminoalcohol of formula XXV, in which $R_{15}$ represents —$CH_2CH_2OH$, is marketed by Eastman Kodak.

The aminoalcohol of formula XXV, in which $R_{15}$ represents

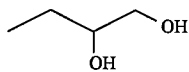

is prepared as described in J. Am. Chem. Soc., 66 881, 1944.

The aminoalcohol of formula XXIV, in which $R_{14}$ represents H, is prepared as described in Propellants, Explos. Pyrotech. 16(1), 40–42, 1991.

The aminoalcohols of general formula:

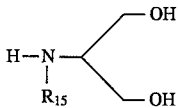

are prepared in the following manner:

$R_{15}$ represents —$CH_3$ (EP 25083);

$R_{15}$ represents —$CH_2CH_2OH$ (EP 25083, J. Med. Chem. 10(3), 511, 1967);

$R_{15}$ represents

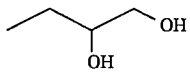

(EP 25083).

The aminoalcohol of formula:

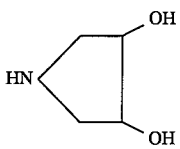

is prepared as described in Angew. Chem. 6, 23, (1984), J. Med. Chem. Z, 1962 (1990).

The aminoalcohol of formula:

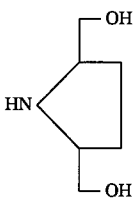

is prepared as described in Tetrahedron Letters, 8, 857 (1984).

The aminoalcohol of formula:

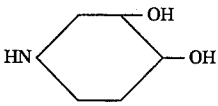

is prepared as described in J. Pharmacy and Pharmacology, 14 306 (1962).

The aminoalcohol of formula:

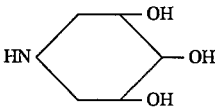

is prepared as described in Chem. Ber., 8, 2467 (1967), Tetrahedron Letters, 15, 2139 (1990).

The aminoalcohol of formula:

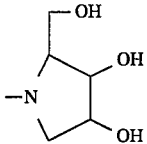

is prepared as described in G. Meng. M. Hesse, Helvetica Chimica Acta, vol. 74, p. 445–450 (1991).

Naturally, the invention encompasses not only the compounds of formula I in the form of racemic mixture. but also stereoisomers such as the enantiomers, diastereoisomers, optical isomers, and isomers SYN-ANTI, ENDO-EXO, E-Z, resulting from presence of asymmetric carbon atoms and/or limited rotation due to the steric hindrance caused by iodine atoms and/or by the substituents $RH_1$, $R_2$ and $R_3$ of the compounds of formula I.

The subject matter of the present invention also the contrast media containing at least one compound of formula I.

These contrast media are used in man and in animals for radiological purposes.

The preferred pharmaceutical forms of the contrast media according to the invention are aqueous solutions of the compounds.

The aqueous solutions generally contain a total of 5 to 100 g of at least one compound of formula I per 100 ml and the injectable quantity of such solutions may generally vary from 1 to 1000 ml.

The aqueous solutions of the compounds of formula I may also contain certain additives such as:

sodium chloride at concentrations of between 0.1 to 10 mM

EDTA disodium salt, at concentrations of between 0.1 and 2 mM sodium citrate at concentrations of between 0.1 and 10 mM heparin in amounts of between 10 and 100 units per 100 ml of solution, and buffer solutions such as tris(hydroxymethyl)aminomethane hydrochloride.

These compositions may be administered by any route conventionally used for iodinated nonionic contrast agents. Thus, they can be administered enterally (orally, rectally) or parentally (intravenously, intraarterially, intraarticularly, opacification of the cavities), and in particular into the subarachnoid space, as well as by the bronchial, lymphatic and intrauterine routes.

In some special uses it may be necessary, in order to perform the diagnosis of a given pathology, especially in a specific organ, to have recourse to what is known as vectorisation of the contrast agent, which may be achieved by encapsulation of the said agent in liposomes or by its binding to a biomolecule, especially proteins.

An example of a composition according to the present invention will be given below.
Composition
Composition of example 2 65 g
Water for injection
qs 100 g The following examples illustrate the preparation of the compounds of formula I

EXAMPLE 1

Preparation of 5-acetamido-N,N'dimethyl-N,N'-bis [2,2-bis(hydroxymethyl)-3-hydroxypropyl]-2,4,6-triiodoisophthalamide of formula: (compound IVa)

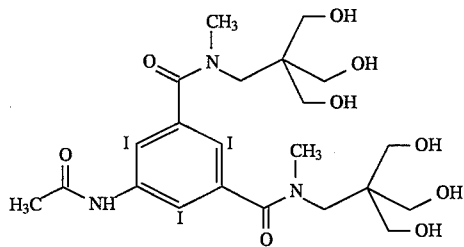

1-Preparation of the compound of formula:

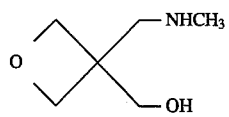

3-hydroxymethyl-3-methylaminomethyloxetane.

16 g (0.088 mol) of 3-bromomethyl-3-hydroxymethyloxetane, prepared according to M. A. Hiskey, Propellants, Explosives, Pyrotechnics, 16, 40–42 (1991), are stirred in 50 ml of ethanol with 69 ml (0.88 mol) of 40% aqueous methylamine, at 80° C., under pressure, for 5 hours. The mixture is evaporated to dryness, then the residue is redissolved in 50 ml of ethanol, and 4.9 g (0.088 mol) of potassium hydroxide are added. After 1 hour, the suspension is filtered and the filtrate is evaporated to dryness. The residue is taken up in 50 ml of dichloromethane. The suspension is filtered and then evaporated to dryness. The residue is distilled (b p: 160° C., at 0.03 bars) and 10.2 g of 3-hydroxpethyl-3-methylaminomethyloxetane are obtained (yield 88.7%).

Analyses:
TLC: (SiO$_2$): CH$_2$Cl$_2$—MeOH 8/2 Rf: 0.3
IR (KBr) 3380, 3300, 2940, 2870, 2800, 1450, 1070, 930 cm$^{-1}$.
NMR:
$^1$H (DMSO-d$_6$)δ:4.27 (s, 4H, CH$_2$ ring), 3.59 (s, 2H, CH$_2$—O), 2.71 (s, 2H, CH$_2$—N), 2.29 (s, 3H, CH$_3$)
$^{13}$C (DMSO-d$_6$)δ:76.27; 64.32; 55.51 (methylene) 44.17 (quaternary), 37.06 (methyl).

2-Preparation of the compound of formula:

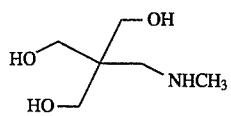

2,2-bis(hydroxymethyl)-3-methylamino-1-propanol(aminoalcohol no. 9)

10 g (0.08 mol) of 3-hydroxymethyl-3-methylaminomethyloxetane are dissolved in 30 ml of water with 6.5 ml of 18N sulphuric acid. The solution is refluxed for 16 hours and then cooled and eluted through anionic resin IRC 50. The eluate is evaporated to dryness and the residue is distilled (b.p.: 180°–190° C., at 0.02 mbar) to give 6 g (yield: 50%) of 2,2-bis(hydroxymethyl)-3-methylaminopropanol.

Analyses:
TLC (SiO$_2$) (methanol/ammonium hydroxide: 8/2)Rf: 0.39
I.R (KBr) 3290, 3250, 2960, 2940, 2880, 1450, 1020 cm$^{-1}$
$^1$H (DMSO-d$_6$)δ4.10 (s, 3H, OH), 3.35 (s, 6H, CH$_2$O), 2.49 (s, 2H, CH$_2$N), 2.27 (s, 3H, CH$_3$)
$^{13}$C (DMSO-d$_6$)δ62.77; 54.05 (methylene), 44.34 (quaternary), 37.32 (methyl).

3-Preparation of 5-acetamido-2,4,6-triiodoisophthaloyl dichloride

To a mixture of 16 ml of acetic anhydride (0.18 mol) and 2 ml of concentrated sulphuric acid are added 5 g of 5-amino-2,4,6-triiodoisophthaloyl chloride (0.008 mol) obtained according to the method described in FR 2, 343, 718. The stirring is continued for 1 hour at room temperature. 3.24 g of product are obtained after filtration, with a yield of 60.6%.

TLC (SiO$_2$),(toluene-acetone: 80/20), Rf 0.37.

4-Preparation of 5-acetamido-N,N'-dimethyl-N,N'-bis-[2, 2-bis(hydroxymethyl)-3-hydroxypropyl]-2,4,6-triiodoisophthalamide 10 g (0.0156 mol) of 5-acetamido-2,4,6-triiodoisophthaloyl dichloride, obtained in the preceding stage, are dissolved in 30 ml of dimethylacetamide containing 6.5 ml (0.047 mol) of triethylamine.

6.9 g (0.047 mol) of 2,2-bis(hydroxymethyl)-3-methylamino-1-propanol, obtained in stage 2 above, are slowly added to the solution, at a temperature of 50° C. The stirring is continued for 6 hours at this temperature, and then the solution is evaporated to dryness. The residue is taken up in water and is eluted through the resins IRN 77 and IRA 67. After evaporation to dryness, 9.5 g of a white powder are obtained (yield 70%).

TLC (SiO$_2$)-butanol/H$_2$O/CH$_3$COOH 50/25/11
Rf: 0.49; 0.53
13CH$_2$Cl$_2$ methanol 8/2
Rf: 0.82.

EXAMPLE 2

Preparation of the compound of formula: (compound Vc)

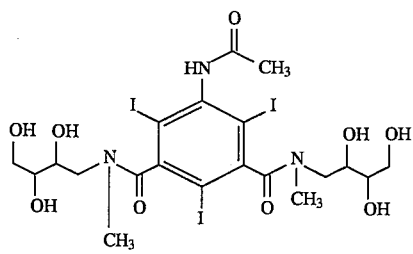

5-acetamido-N,N'-dimethyl-N,N'-bis(2,3,4-trihydroxybutyl)-2,4,6-triiodoisophthalamide.

1.2 g (1.85 mmol) of 5-acetamido-2,4,6-triiodoisophthaloyl dichloride, as described in Example 1–3) above, is added to a solution of 1 g (7.4 mmol) of the aminoalcohol no. 1 prepared according to the method described above, and triethylamine (7.4 mmol) in 7 ml of dimethylacetamide. The stirring is continued for minutes at 40° C. The triethylamine hydrochloride is removed by filtration.

The filtrate is evaporated to dryness, taken up in water and eluted through the resins IRN 77 and IRA 67. After evaporation to dryness, 1.32 g of a white powder are recovered (yield 84%).

Iodine assay: 99.5%

HPLC purity: 99% Lichrosphere C$_{18}$ 5 μm 0.01M NaH$_2$PO$_4$ MeOH

TLC (SiO$_2$) CH$_2$Cl$_2$/MeOH: 70/30, Rf: 0.33, 0.26, 0.58 dioxane/water/NH$_3$: 80/30/20, Rf 0.74

$^1$H NMR (DMSO) 200 MHz (δ,ppm): (2.1, s, 3H, NHCO CH$_3$); (2.85, s, 6H, N—CH$_3$); (3,1–4, broad 12H, CH and CH$_2$); (4.3–4.9, un-broad 6H, OH) (10, broad 1H, NH)

$^{13}$C (δ,ppm): (22.28, NHCO$\underline{C}$H$_3$); (37.76, N—$\underline{C}$H$_3$); (50.58, N—$\underline{C}$H$_2$); (62.35, $\underline{C}$H$_2$OH); (69.89–73.4, $\underline{C}$HOH); (89.45–97.4–98.8, 2C—I) (143.69, $\underline{C}_{ar}$—N); (148–148.6. $\underline{C}_{ar}$—CO) (171.9–172.1, $\underline{C}$=O).

EXAMPLE 3

Preparation of the compound of formula: (compound Vb)

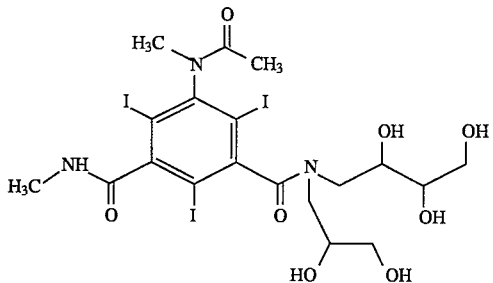

[N-(2,3-dihydroxypropyl)-N-(2,3,4-trihydroxybutyl)]-3-(N'-methyl)-5-N-methylacetamido-2,4,6-triiodoisophthalamide.

1 g (1.54 mmol) of 5-N-methylacetamido-2,4,6-triiodo-N-methylbenzamide chloride prepared according to the method described in FR 2,272,640, is added to a solution of 542 mg (3.09 mmol) of the aminoalcohol no. 2 obtained according to the method described above, and triethylamine (3.09 mmol) in 7 ml of dimethylacetamide. The stirring is continued for 4 hours at 60° C.

The solution is then concentrated by distillation. After purification with the resins IRN 77 and IRA 67 and evaporation to dryness, 1 g of a white powder is obtained (yield: 82%).

TLC (SiO$_2$)CH$_2$Cl$_2$/MeOH: 7/3: Rf 0.58 dioxane/H$_2$O/ NH$_3$: 80/30/20 Rf: 0.89

$^{13}$C NMR 200 MHz (δ,ppm): (24.22, N—$\underline{C}$H$_3$); (25.73, CO$\underline{C}$H$_3$); 33.65, NHCH$_3$); (49.63–53.54, N(CH$_2$)$_2$); (61.8–63.3, $\underline{C}$H$_2$OH); (68.64–73.28, $\underline{C}$HOH); (90,56–98,01, $\underline{C}$—I); (147.9–148.1, $\underline{C}$—CO); (150.33, $\underline{C}_{ar}$—N); (171.6–172.9, $\underline{C}$=O).

EXAMPLE 4

Preparation of the compound of formula: (compound IIa)

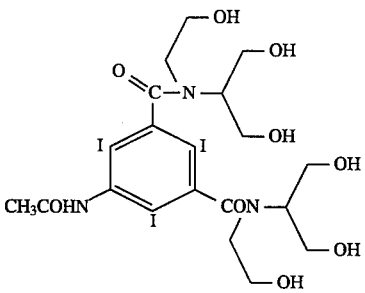

5-acetamido-N,N'-bis(2-hydroxymethyl)-N,N'-bis[1-hydroxymethyl)-(2-hydroxy)ethyl]-2,4,6-triiodoisophthalamide To 4.17 g (6.94 mmol) of 5-acetamido-2,4,6-triiodoisophthaloyl dichloride, obtained according to the method described in Example 1–3 above, is slowly added a solution of 3.53 g (0.026 mmol) of the aminoalcohol

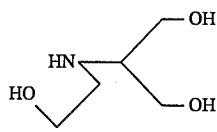

obtained according to the process described in EP 25083 and J. Med. Chem. 10/3, 511, 1967, and 2.63 g of triethylamine in 20 ml of dimethylacetamide.

The stirring is continued for 48 hours at 50° C. The excess triethylamine and N,N-dimethylacetamide is removed by distillation. The residue is taken up in water and passed through $H^+$ and $OH^-$ ion-exchange resins. After evaporation and crystallisation, 3.5 g of product are obtained (yield: 64%).

TLC ($SiO_2$):dioxane/$H_2O$/$NH_3$: 80/30/20, Rf: 0.8

HPLC purity: 99% Lichrosphere $C_{18}$ 5 μm Buffer MeOH $^{13}C$ NMR (DMSO) (δ,ppm):
(23.02, $\underline{C}OCH_3$); (50, —N—$\underline{C}H_2$—$CH_2OH$) ;(59.30, CH($\underline{C}H_2OH)_2$); (62 $\underline{C}$ H($CH_2HO)_2$); (92–100 3$\underline{C}$—I); (145–148 $\underline{C}_{ar}$—N and $\underline{C}_{ar}$—CO); (167–170, $\underline{C}$=O).

EXAMPLE 5

Preparation of the compound of formula: (compound VIb)

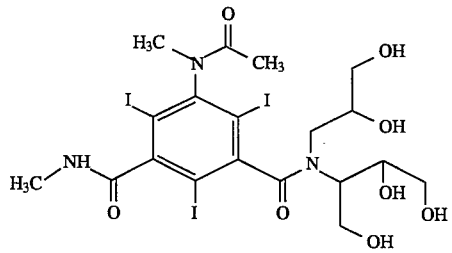

1 g (1.54 mmol) of 5-N-methylaceteido-2,4,6-triiodo-3-N-methylaminocarbonylbenzamide chloride, prepared according to the method described in FR-2,272,640, is added to a solution of 542 mg (3.09 mmol) of the einoalcohol no. 5 obtained according to the method described above, and triethylamine (3.09 mmol) in 5 ml of dimethylaceteide. The stirring is continued for 48 h at 65° C.

The solution is concentrated by distillation. After purification through the resins $H^+$ IRN 77 and $OH^-$ IRA 67, and evaporation to dryness, the title product is obtained in the form of a white powder.

TLC ($SiO_2$) $CH_2Cl_2$—MeOH 7/3, Rf: 0.49 dioxane/$H_2O$/$NH_3$ 80/30/20, Rf: 0.8.

EXAMPLE 6

Preparation of the compound of formula: (compound Ve)

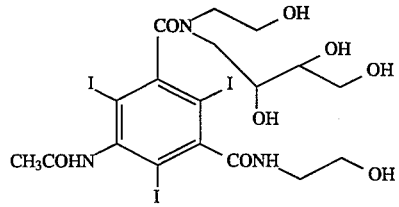

5-acetamido-3-(N'-2-hydroxyethyl)-N-(2-hydroxyethyl-2',3',4'-trihydroxybutyl)-2,4,6-triiodoisophthalamide To 675 ml (7.15 mol) of acetic anhydride, heated to 50° C., are slowly added 250 g (0.42 mol) of 3-(N-hydroxyethylcarbamoyl)-5-amino-2,4,6-triiodobenzoic acid, obtained according to the method described in patent FR 6777.M.

The temperature is maintained around 55° C. during the addition of 1.5 ml of perchloric acid.

The stirring is continued for 8 hours at 50° C. After distillation under reduced pressure, 380 ml of butyl acetate are added after cooling. The reaction medium is neutralised by adding 1.5 g of sodium acetate and stirring is continued for 12 hours at room temperature. The medium is then heated to 70° C. and 168 ml (2.34 mol) of thionyl chloride are slowly added while the heating is maintained for 2 hours. The thionyl chloride and the acetyl chloride generated are then removed by distillation under reduced pressure.

The residue is taken up in 150 ml of butyl acetate, and then stirred for 3 hours at 10° C. The product is filtered, rinsed with butyl acetate and drained.

Yield: 78%

TLC (toluene/methyl ethyl ketone/formic acid: 65/35/25) Rf: 0.7

$^1H$ NMR ((DMSO-$d_6$):2 ppm (s, 33H);2.15 (s, 3H); 2.35 (s, 3H) 3.5 (b, 2H); 4.15 (b, 2H); 9.8 (b, 1H).

100 g (133.9 mmol) of 5-N,N-diacetylamino-3-(N'-2-acetoxyethyl)carbamoyl-2,4,6-triodobenzoic acid chloride, obtained in the preceding stage, are added to a solution of 44.2 g (268 mmol) of the aminoalcohol no. 3 obtained according to the method described above, and triethylamine (268 mmol) in 220 cm$^3$ of dimethylacetamide. The stirring is continued for 2 hours at 55° C. Triethylamine hydrochloride is removed by filtration and the filtrate is evaporated to dryness. The residue is diluted in 500m 1 of water and contacted with 2N NaOH (180 ml) for 12 hours. The solution is then neutralised and eluted through resins IRN 77 and IRA 67.

After evaporation to dryness, 58.4 g of product are obtained, equivalent to a yield of 55%.

TLC: ($SiO_2$) $CH_2Cl_2$/MeOH/$NH_3$: 8/3/2 Rf: 0.27+0.41

Iodine assay: 98.4%

HPLC purity: 99.5% (Raw) 95%

Lichrosphere $C_{18}$5 μm; $NaH_2PO_4$ 0,01M; MeOH $^1H$ NMR (DMSO) 200 MHz (δ,ppm): (2.01, S, 3H, NHCO$\underline{C}H_3$); (3.85–4.15; broad 14H, C$\underline{H}$ and C$\underline{H}_2$; (4.3–5.1 broad 5H, O$\underline{H}$); (8.5, broad 1H, ArCON$\underline{H}$); (9.9, broad 1H, ArN$\underline{H}$CO).

EXAMPLE 7

Preparation of the compound of formula:

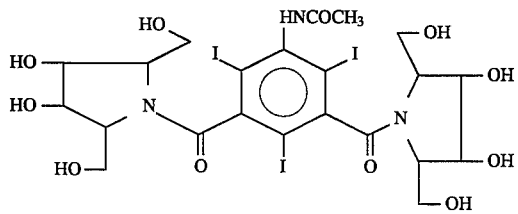

1,3-bis[(2S,5S)-dihydroxymethyl)-(3R,4R)-dihydroxy-pyrrolidin-1-yl-carbonyl]-5-acetamido-2,4,6-triiodophenyl.

28.45 G (0.1745 mol) of (2S,5S)-dihydroxymethyl-(3R, 4R)-dihydroxypyrrolidine are stirred in the presence of 24.5 cm$^3$ of triethylamine and 200 cm$^3$ of DMAC at 50° C. 31.82 g (0.05 mol) of 5-acetamido-2,4,6-triiodoisophthaloyl chloride, as prepared in Example 1–3 above, are slowly added and the reaction is maintained at 50° C. for 48 hours. The DMAC is then evaporated and the reaction medium is taken up in dichloromethane, filtered and then evaporated. The oil is then diluted to a volume of 200 cm$^3$ and then passed through H$^+$ and OH$^-$ ion-exchange resins. The aqueous phase is evaporated to dryness. The product is obtained, after drying in an oven and purification by preparative HPLC, with a yield of 23%.

TLC (CHCl$_3$ 55/MeOH45/NH$_4$OH10): Rf=0.14; 0.2

Iodine purity: 100.1%

H$_2$O content 2%

HPLC purity: 99%

$^1$H NMR (DMSO): δ: 10.0 (b. 1H, NH), 5.5 (b 8H, OH) 4 to 2.8 (b. 16H, CH$_2$—CH) 2.0 (1. 3H, CH$_3$)

$^{13}$C NMR (D$_2$O+C$_6$H$_6$ standard): δ: 172 (C=O, NHCO), 170.0 (C=O, CO—N); 147.6–147.1–143.1 (C9); 101.1–98, 8–91.3 (CI); 72.7–72.5 (CHOH); 59.8–59.3 (CH—N); 58.4–56.9 (CH$_2$—OH); 21.7 (CH$_3$).

EXAMPLE 8

Preparation of the compound of formula:

for 4 hours and left at room temperature overnight. The reaction medium is filtered. The precipitate is passed through H$^+$ and OH$^-$ resins, taken up in absolute ethanol and then in water, evaporated to dryness and dried (yield 63%).

Analysis: TLC (SiO$_2$) CH$_2$Cl$_2$–MeOH (4/6) visualisation: UV

Rf: 0.27

Iodine purity: 99.43% $^1$H NMR (DMSO)δ: 12.0 (b, 2H, NH), 4.6 to 4.4 (b,12H, OH), 3.8 (b, 4H, CHOH), 3.5 (b, 8H, CH$_2$OH), 3.4 (b 2H, CH$_2$, 3.2 (b, 8H, NCH$_2$), 3.1 to 2.6 (b, 12H, CH$_3$);

$^{13}$C (D$_2$O+C$_6$H$_6$ standard δ: 171 (C=O, N—C=O), 166 (C=O, N—C=O), 148–147 (C cycl., C—C=O), 142 (C cycl., C—NH), 98 to 86 (C cycl., CI), 72 to 69 (CH, CHOH), 61 (CH$_2$, CH$_2$OH), 50 (CH$_2$, N—CH$_2$), 37 to 33 (CH$_3$, N—CH$_3$)

MS (FAB): correct; M+1=1655

EXAMPLE 9

Preparation of the compound of formula

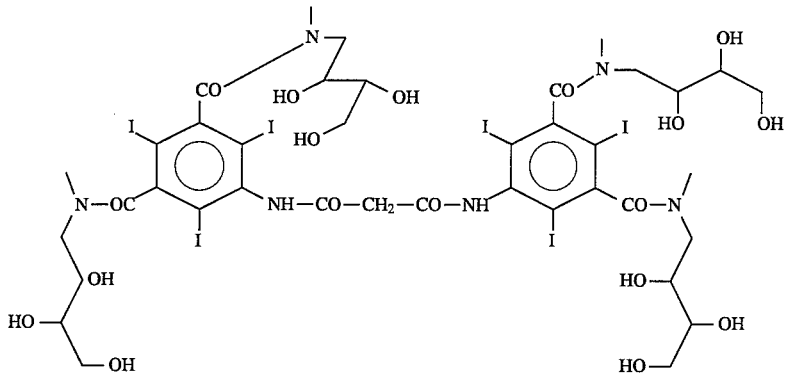

A mixture of 36.50 g (0.27 mol) of N-methylaminobutanetriol (aminoalcohol no. 1), 27.27 g (0.27 mol) of triethylamine and 400 ml of isopropanol are heated to 40° C.

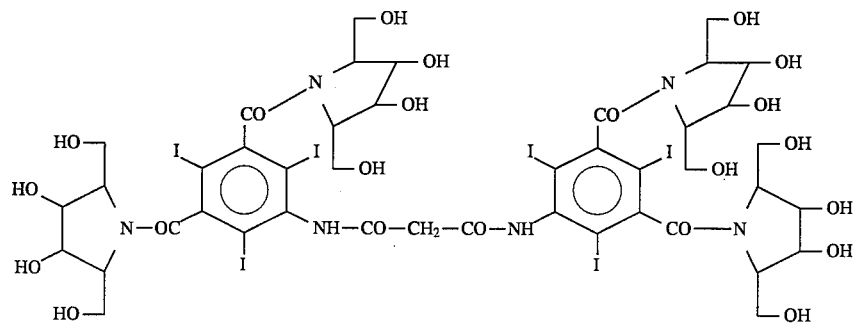

TO this mixture are added 71.70 g (0.057 mol) of bis[3,5-bis(chlorocarbonyl)-2,4,6-triodophenyl]malonamide, prepared according to the method described in patent U.S. Pat. No. 4,426,371 in the name of SCHERING AG, dissolved in 415 ml of isopropanol. The solution is maintained at 40° C.

A mixture of 1.01 g (6.13 mmol) of (2S,5S)-bishydroxymethyl-(3R,4R)-bishydroxypyrrolidine prepared according to the method described in Tetrahedron Letters, 31, 6777 (1990), J. Org. Chem. 50, 892 (1985), of 0.62 g (6.13 mmol) of triethylamine and of 3 ml of N,N-dimethylacetaide is heated to 50° C. To this mixture is added 0.88 g (0.70 mmol) of bis[3,5-bis(-chlorocarbonyl)-2,4,6-triiodophenyl]malonamide, prepared according to the method described in U.S. Pat. No. 4,426,371, dissolved in 2.5 ml of N,N-dimethylacetaide. The solution is maintained at 50° C. for 24 hours and left at room temperature overnight. The reaction medium is filtered. The filtrate is passed through resins H⁺ and OH⁻, taken up in absolute alcohol then in water and evaporated to dryness and dried. 380 mg of a white powder are isolated.

Analysis

HPLC (70 $CH_3OH$/30 $H_2O$) $t_R$=1.62 column C18.

EXAMPLE 10

Preparation the compound of formula: (compound Vd):

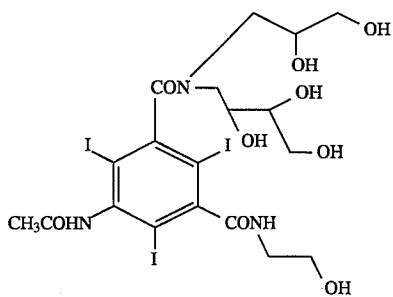

5-acetamido-3-(N-2-hydroxyethyl)-1-N'-(2,3,4-trihydroxybutyl-2', 3',-dihydroxypropyl)-2,4,6-triiodo-isophthalamide:

100 g (133.9 mmol) of 5-N,N-diacetylamino-3-N'-(2-acetoxyethyl)carbamoyl-2,4,6-triiodobenzoic acid chloride, prepared according to the method described in Example 6 above, are added to a solution of 39.2 g (200 mmol) of the aminoalcohol no. 2 obtained according to the method described above, and triethylamine (267.8 mmol) in 220 ml of dimethylacetamide. The stirring is continued for two hours at 55° C. The triethylamine hydrochloride is removed by filtration. The filtrate is evaporated to dryness. The residue obtained, diluted in 500 ml of water, is contacted with 2N sodium hydroxide (120 ml) for 12 hours.

The medium is then neutralised before being successively passed through the resins IRN 77 and IRA 67. After evaporation to dryness, 58.5 g of the compound Vd are obtained, equivalent to a yield of 53%.

TLC ($SiO_2$)$CH_2Cl_2$/MeOH / $NH_3$: 7/3/2 Rf: 0.28

Iodine assay: 99.2%

Purity HPLC: (Lichrosphere $C_{18}$ 5 μm $NaH_2PO_4$: 0.01M, MeOH): 99%

¹H NMR (DMSO) 200 MHz (δppm). (2.01; δ; 3H ; NHCOC$\underline{H}_3$); (3–4.2 ; broad 15H; C$\underline{H}$ and C$\underline{H}_2$); (8.5; broad, 1H, ArCON$\underline{H}$); (9.9: broad, 1H, ArN$\underline{H}$CO).

We claim:

1. Polyiodinated nonionic compound of formula:

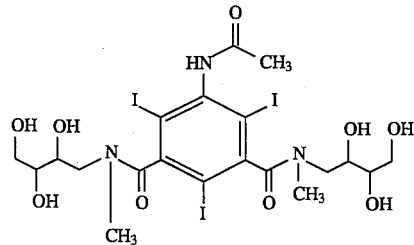

2. Contrast media comprising the compound according to claim 1.

3. Contrast media according to claim 2, comprising an aqueous solution of the compound.

* * * * *